United States Patent
Lu et al.

(10) Patent No.: US 11,219,475 B2
(45) Date of Patent: Jan. 11, 2022

(54) DEVICE FOR SURGERY TO STABILIZE BONE SEGMENTS, EXTENDING ASSEMBLY AND ASSEMBLING METHOD THEREOF

(71) Applicant: WILTROM CO., LTD., Zhubei (TW)

(72) Inventors: Chieh-Feng Lu, Zhubei (TW); Yi-Chun Su, Zhubei (TW)

(73) Assignee: WILTROM CO., LTD., Zhubei (TW)

( * ) Notice: Subject to any disclaimer, the term of this patent is extended or adjusted under 35 U.S.C. 154(b) by 55 days.

(21) Appl. No.: 16/594,675

(22) Filed: Oct. 7, 2019

(65) Prior Publication Data

US 2020/0107865 A1   Apr. 9, 2020

(30) Foreign Application Priority Data

Oct. 9, 2018   (TW) ................................. 107135609

(51) Int. Cl.
*A61B 17/70*   (2006.01)

(52) U.S. Cl.
CPC ................................ *A61B 17/7074* (2013.01)

(58) Field of Classification Search
CPC ............ A61B 17/7074; A61B 17/7077; A61B 17/708; A61B 17/7083; A61B 17/7085; A61B 17/7075; A61B 17/7001; B65D 41/0471; B65D 43/022; B65D 43/0229; B65D 45/327
See application file for complete search history.

(56) References Cited

U.S. PATENT DOCUMENTS

| | | | | |
|---|---|---|---|---|
| 1,304,098 | A * | 5/1919 | Rives ................. | B65D 41/0471 215/331 |
| 7,588,575 | B2 * | 9/2009 | Colleran ................. | A61B 5/103 606/252 |
| 8,388,659 | B1 * | 3/2013 | Lab ..................... | A61B 17/7037 606/265 |
| 8,870,919 | B2 * | 10/2014 | Miller ................ | A61B 17/7037 606/246 |
| 2009/0221878 | A1 * | 9/2009 | Gorek ................ | A61B 17/0293 600/206 |
| 2018/0070987 | A1 * | 3/2018 | Su ...................... | A61B 17/8875 |
| 2018/0263675 | A1 * | 9/2018 | Erramilli ............ | A61B 17/7074 |
| 2019/0069930 | A1 * | 3/2019 | Su ...................... | A61B 17/7032 |
| 2019/0365423 | A1 * | 12/2019 | Arnold ............... | A61B 17/7082 |

\* cited by examiner

*Primary Examiner* — Julianna N Harvey
*Assistant Examiner* — Holly Joanna Lane
(74) *Attorney, Agent, or Firm* — Muncy, Geissler, Olds & Lowe, P.C.

(57) ABSTRACT

The present disclosure discloses a device for surgery to stabilize bone segments, which includes a screw assembly, a supporting member, an extending member, and a fastening member. The supporting member is connected with an arm of a receiver of the screw assembly. The extending member includes a connecting portion and an extending portion. The connecting portion is located at one end of the extending member opposite to the receiver. The extending portion is connected to the arm with the supporting member passing through a through hole of the extending portion, and a portion of the supporting member protrudes out of the extending portion to the connecting portion. The fastening member is sleeved on the connecting portion and has a pressing groove. The supporting member is located between the connecting portion and the pressing groove. The pressing groove includes a release position and a pressing position for the supporting member.

20 Claims, 13 Drawing Sheets

DEVICE FOR SURGERY TO STABILIZE BONE SEGMENTS, EXTENDING ASSEMBLY AND ASSEMBLING METHOD THEREOF

BACKGROUND OF THE DISCLOSURE

1. Field of the Disclosure

The present disclosure relates to a device for surgery to stabilize bone segments, and an extending assembly, fastening member and assembling method thereof.

2. Description of the Related Art

The vertebral column is a major component of the central nervous system of the human body. Spinal disorders, especially in the lumbar region, often have a considerable impact on patients, causing pain, numbness, weakness, incontinence, dysuria, dyschezia, or other symptoms. The above symptoms are caused by a displacement of vertebrae putting pressure on the nerve or spinal cord. Due to different mechanisms, spinal disorders are clinically diagnosed as spinal disc herniation, spondylolisthesis, spinal stenosis or degenerative scoliosis. When symptoms are severe, the discomfort of patients usually cannot be relieved by correction, and spinal surgery is required to reposition the vertebrae. An important key to treatment success is the effective fixation of the repositioned vertebral body to prevent recurrent displacement.

The pedicle screw fixation system, a spinal implant device applied in vertebral fusion surgery, is the most stable and prevalent treatment for vertebral repositioning and fixation in traditional intervertebral disc resection, cervical degeneration and scoliosis correction. The pedicle screw fixation system includes a plurality of pedicle screws (also known as a screw assembly). The pedicle screw can be a monoaxial or polyaxial pedicle screw, but the use of a polyaxial pedicle screw is more convenient. In the case of a polyaxial pedicle screw, as shown in FIG. 1B, each pedicle screw 9 generally includes a screw shaft, a receiver (also known as a tulip) and a locking nut (also known as a nut, not shown in the figure). A common surgical procedure of the pedicle screw fixation system involves a first step of inserting pedicle screws in pairs into the pedicles of each vertebra from both sides of the spinous process of the vertebra. After that, rods are adjusted in advance in accordance with the normal vertebral curve, and then the locking screws are tightened into the receiver by particular surgical instruments such as a pre-lock wrench and an anti-torque wrench to fix the rods within the receivers. Once the rods are fixed within the receivers, two adjacent vertebrae are correspondingly repositioned or stabilized.

Traditional spinal surgery is an open-type approach in which a midline incision is made in the back of the patient. The muscle tissue is cut open and then moved aside to expose the vertebrae, and the periosteum is peeled off from the vertebral section prior to the installation of the pedicle screw fixation system. The problems of this procedure are the large wound and the high blood loss; moreover, due to the invasive nature of the surgery, the recovery of the wound is a slow process. Furthermore, the reduced elasticity and fibrosis in the muscle tissue after surgery usually cause severe soreness, pain, and high risk of infection. These problems extend the length of the hospital stay and increase the overall medical expenses, which are problems that have to be solved in terms of public health policy. Therefore, in recent years, minimally invasive surgery (MIS), which can significantly reduce the size of surgical wounds, has been gradually favored by surgeons and patients, and its clinical importance is also increasing.

Generally, a minimally invasive surgery is defined as one in which a surgical wound is less than 3 cm and anatomical damage is avoided as much as possible; however, when the surgery is performed, the tightness of the muscles around the incision restrict the size of the operative field or obstruct the operation of the surgical instruments. In a minimally invasive surgery, an extending member or sleeve is usually provided to maintain the operative path. Specifically, the surgery is performed via small incisions on the back of the patient corresponding to the positions of the pedicles on the two sides of the vertebral process. The pedicle screw provided with the extending members or the sleeve is implanted in the vertebral body to maintain the operative path such that the surgical instruments can be operated on the pedicle screw with a sufficient operative field and no obstruction to finish the installation of the pedicle screw fixation system. However, the general extending member is connected to the receiver only by a simple snap structure, and the sleeve is directly clamped or sleeved on the outside of the receiver; thus, the stability of these connection methods is not good. If any external force is applied, the extending member or the sleeve can very easily be skewed, slip, or even be loosened. Therefore, some manufacturers have tried to improve the connection stability of the extending member and the receiver by adding the design of a supporting member.

FIG. 1A illustrates a schematic view of a conventional pedicle screw having an extending member and a supporting member, and FIG. 1B illustrates an explosive view of the extending member and the pedicle screw shown in FIG. 1A. Referring to FIG. 1A and FIG. 1B, this type of pedicle screw 9 includes a screw shaft 91 and a receiver 92, and the receiver 92 is U-shaped and has two arms 921. The supporting member 8 is disposed on the top surface of the arms 921 and extends in the longitudinal axis direction Y. The extending member 7 has a through hole 71, through which one end of the extending member 7 is interconnected with the arms 921 after passing through the supporting member 8. The connection stability of the extending member 7 and the receiver 92 is improved by the design of the supporting member 8. In order to avoid displacement of the supporting member 8 in the through hole 71 and to prevent the extending member 7 from being loosened, a fastening structure 72 is further provided to the extending member 7.

FIG. 1C illustrates a schematic cross-sectional view taken along line A-A of FIG. 1B. As shown in FIG. 1C, the extending member 7 has side holes adjacent to the fastening structure 72 so that the supporting member 8 can be exposed from the side holes and in contact with the fastening structure 72. By the curved design of the surface of the fastening structure 72, when the fastening structure 72 is rotated, the fastening structure 72 can interfere with the supporting member 8 to press the supporting member 8 tightly to the through hole 71 to fix the relative position of the supporting member 8 and the extending member 7. In this type of fastening structure, the fastening structure 72 has to be rotated separately at the two sides of the fastening structure 72, and the fastening structure 72 is disposed outside the extending member 7.

SUMMARY

In view of the above problems, it is an object of the present disclosure to provide a device for surgery to stabilize bone segments, and an extending assembly, fastening member, and assembling method thereof. The device comprises a screw assembly, at least one supporting member, an extending member, and a fastening member, and the supporting member is connected to the receiver of the screw assembly. The extending member can pass through the supporting member, and a portion of the supporting member protrudes out of the extending portion to the connecting portion. Since the fastening member is sleeved on the connecting portion and the fastening member is rotated to press the supporting member through the pressing groove, the present disclosure not only stabilizes the relative positions of the extending member and the supporting member but also prevents the overall outer diameter of the device from being greatly increased, and the present disclosure provides rotation operation, which is quite convenient.

In order to achieve the above object, the present disclosure provides a device for surgery to stabilize bone segments. The device comprises a screw assembly, at least one supporting member, an extending member, and a fastening member. The screw assembly comprises a receiver and an anchoring member. The receiver has a retainer and two opposite arms. The anchoring member is connected to the retainer. The supporting member is connected to one of the arms and extends in a longitudinal axis direction of the device. The extending member comprises a connecting portion and at least one extending portion. The connecting portion is located at one end of the extending member opposite to the receiver. The extending portion has a through hole, wherein the extending portion is connected to the two arms with the supporting member passing through the through hole, and a portion of the supporting member protrudes out of the extending portion to the connecting portion. The fastening member is sleeved on the connecting portion, and the fastening member has at least one pressing groove, wherein the supporting member is located between the connecting portion and the pressing groove and the pressing groove comprises a release position and a pressing position for the supporting member. When the fastening member is rotated relative to the connecting portion, the supporting member moves relative to the fastening member and moves along the pressing groove between the release position and the pressing position.

In order to achieve the above object, the present disclosure provides an extending assembly for use in a device for surgery to stabilize bone segments. The device comprises a screw assembly and at least one supporting member. The screw assembly comprises a receiver. The receiver has a retainer and two opposite arms, and the supporting member is connected to one of the two arms and extends in a longitudinal axis direction of the device. The extending assembly comprises an extending member and a fastening member. The extending member comprises a connecting portion and at least one extending portion. The connecting portion is located at one end of the extending member opposite to the receiver. The extending portion has a through hole, wherein the extending portion is connected to the two arms with the supporting member passing through the through hole, and a portion of the supporting member protrudes out of the extending portion to the connecting portion. The fastening member is sleeved on the connecting portion, and the fastening member has at least one pressing groove, wherein the supporting member is located between the connecting portion and the pressing groove. The pressing groove comprises a release position and a pressing position for the supporting member. When the fastening member is rotated relative to the connecting portion, the supporting member moves relative to the fastening member and moves along the pressing groove between the release position and the pressing position.

In order to achieve the above object, the present disclosure further provides a fastening member for use in a device, the device comprising at least one supporting member and an extending member and the extending member comprising a connecting portion and at least one extending portion. The extending portion has a through hole, the supporting member passes through the through hole, and a portion of the supporting member protrudes out of the extending portion to the connecting portion. The fastening member is sleeved on the connecting portion, and the fastening member comprises at least one pressing groove, wherein the supporting member is located between the connecting portion and the pressing groove. The pressing groove comprises a release position and a pressing position for the supporting member. When the fastening member is rotated relative to the connecting portion, the supporting member moves relative to the fastening member and moves along the pressing groove between the release position and the pressing position.

According to an embodiment of the present disclosure, the fastening member is ring-shaped and has a round opening, and the round opening is in communication with the pressing groove.

According to an embodiment of the present disclosure, the round opening has a center point, and the distance between the release position and the center point is greater than the distance between the pressing position and the center point.

According to an embodiment of the present disclosure, the fastening member is sleeved on the connecting portion through the round opening.

According to an embodiment of the present disclosure, a reference arc is defined between the pressing groove and the round opening, and a ratio of the arc length of the reference arc to a circumference of the round opening is between ⅙ and ⅖.

According to an embodiment of the present disclosure, the ratio of the arc length of the reference arc to the circumference of the round opening is ⅜.

According to an embodiment of the present disclosure, an angle between the line connecting the pressing position and the center point and the line connecting the release position and the center point is greater than 14 degrees.

According to an embodiment of the present disclosure, the pressing groove further has a starting point and an end point, the starting point and the end point are respectively located at opposite ends of the pressing groove, the starting point is at a position having a maximum distance between the inner side of the fastening member and the center point, and the end point is at a position having a minimum distance between the inner side of the fastening member and the center point.

According to an embodiment of the present disclosure, the supporting member protrudes a predetermined length from a surface of the connecting portion, the predetermined length is set such that the maximum distance is greater than a sum of a radius of the round opening and the predetermined length, and the minimum distance is substantially equal to the radius of the round opening.

According to an embodiment of the present disclosure, the pressing groove is formed on the inner side of the fastening member, and the distance between the pressing groove and the center point gradually decreases from the starting point to the end point.

According to an embodiment of the present disclosure, the device for surgery to stabilize bone segments further comprises an anchoring cap sleeved on the connecting portion.

According to an embodiment of the present disclosure, the connecting portion further comprises at least one limiting groove in communication with the through hole of the extending portion, and the supporting member is partially covered in the limiting groove.

According to an embodiment of the present disclosure, the extending member comprises two extending portions connected to the two arms respectively.

According to an embodiment of the present disclosure, the extending member has a plurality of side through holes, and the plurality of side through holes are arranged mutually parallel to each other at the extending portion and are in communication with the through hole.

According to an embodiment of the present disclosure, the extending assembly further comprises an anchoring cap that is sleeved on the connecting portion.

In order to achieve the above object, the present disclosure further provides an assembly method for a device for surgery to stabilize bone segments, the device comprising a screw assembly, at least one supporting member, an extending member, and a fastening member. The screw assembly comprises a receiver having a retainer and two opposite arms. The extending member comprises a connecting portion and at least one extending portion, and the extending portion has a through hole. The fastening member has at least one pressing groove. The assembly method comprises the following steps: providing the screw assembly having the supporting member, wherein the supporting member is connected to one of the two arm and extends in a longitudinal axis direction of the device; providing the extending portion to be connected to the two arms with the supporting member passing through the through hole, wherein a portion of the supporting member protrudes out of the extending portion to the connecting portion; providing the fastening member to be sleeved on the connecting portion, wherein the supporting member is located between the connecting portion and the pressing groove; rotating the fastening member relative to the connecting portion; and moving the supporting member relative to the fastening member to be moved along the pressing groove between the release position and the pressing position.

According to the present disclosure, when the fastening member is rotated relative to the connecting portion, the supporting member moves relative to the fastening member along the pressing groove between the release position and the pressing position. When the supporting member moves to the pressing position, the pressing groove gradually increases the pressure on the supporting member such that the resistance between the supporting member and the extending member is gradually increased, and the effect of the fixing is improved. Preferably, the relative displacement between the supporting member and the extending member is less likely to occur, so the extending member is not separated from the screw assembly.

Furthermore, since the mechanism design of the fastening member is rotatably sleeved on the connecting portion of the connecting portion, the outer diameter of the device will not be increased or will be increased slightly, which is beneficial to minimally invasive surgeries.

DETAILED DESCRIPTION OF THE PREFERRED EMBODIMENT

In order to make the structure and characteristics as well as the effectiveness of the present disclosure further understood and recognized, the detailed description of the present disclosure is provided as follows along with embodiments and accompanying figures.

First, the device for surgery to stabilize bone segments in the present disclosure is described using the embodiment of a pedicle screw of a pedicle screw fixation system used in minimally invasive spinal surgery as an example. But it should be known to those skilled in the art that the device of the present disclosure is not limited to the pedicle screw or to the use in minimally invasive spinal surgery.

Figure 1A:
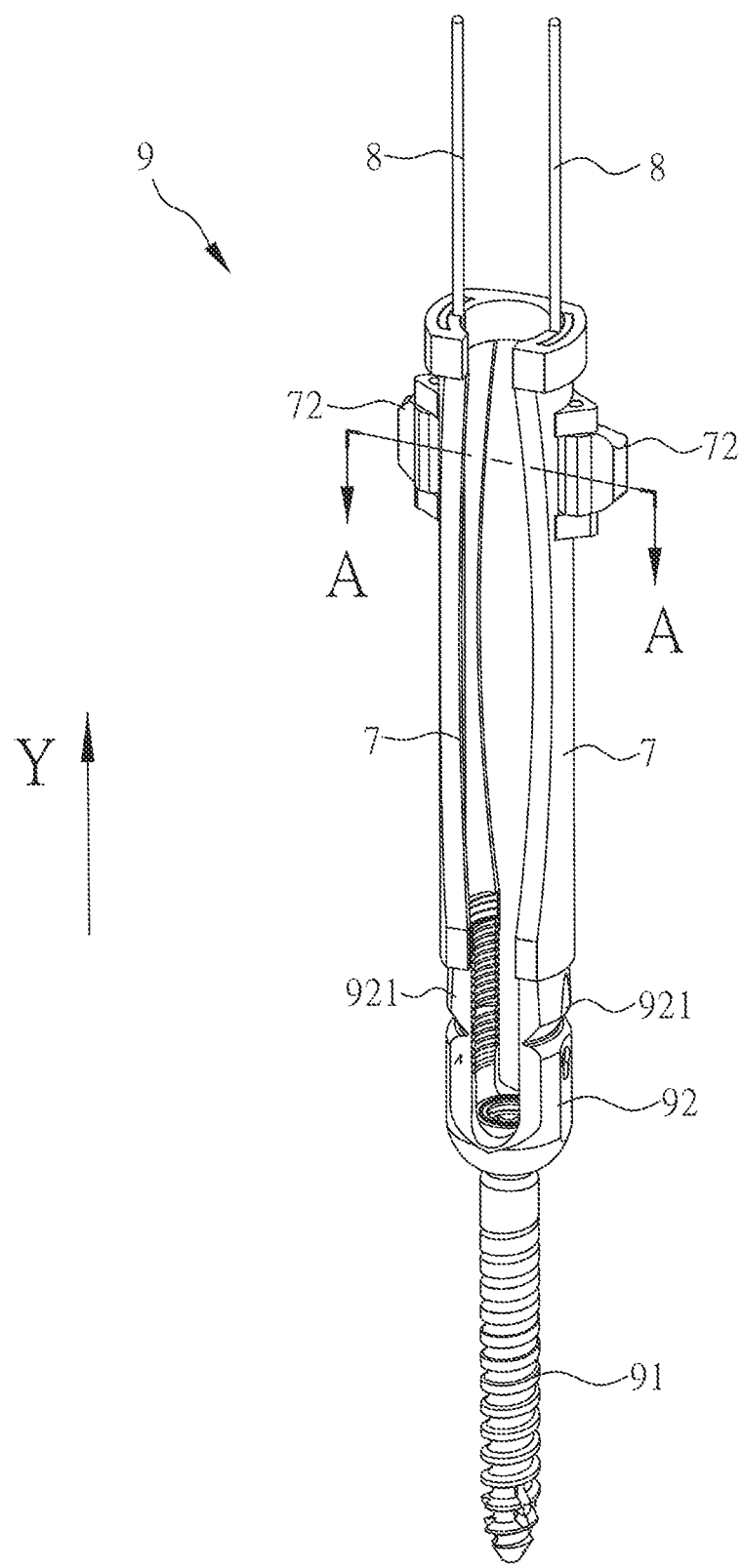
FIG. 1A illustrates a schematic view of a conventional pedicle screw having an extending member and a supporting member.
Figure 1B:
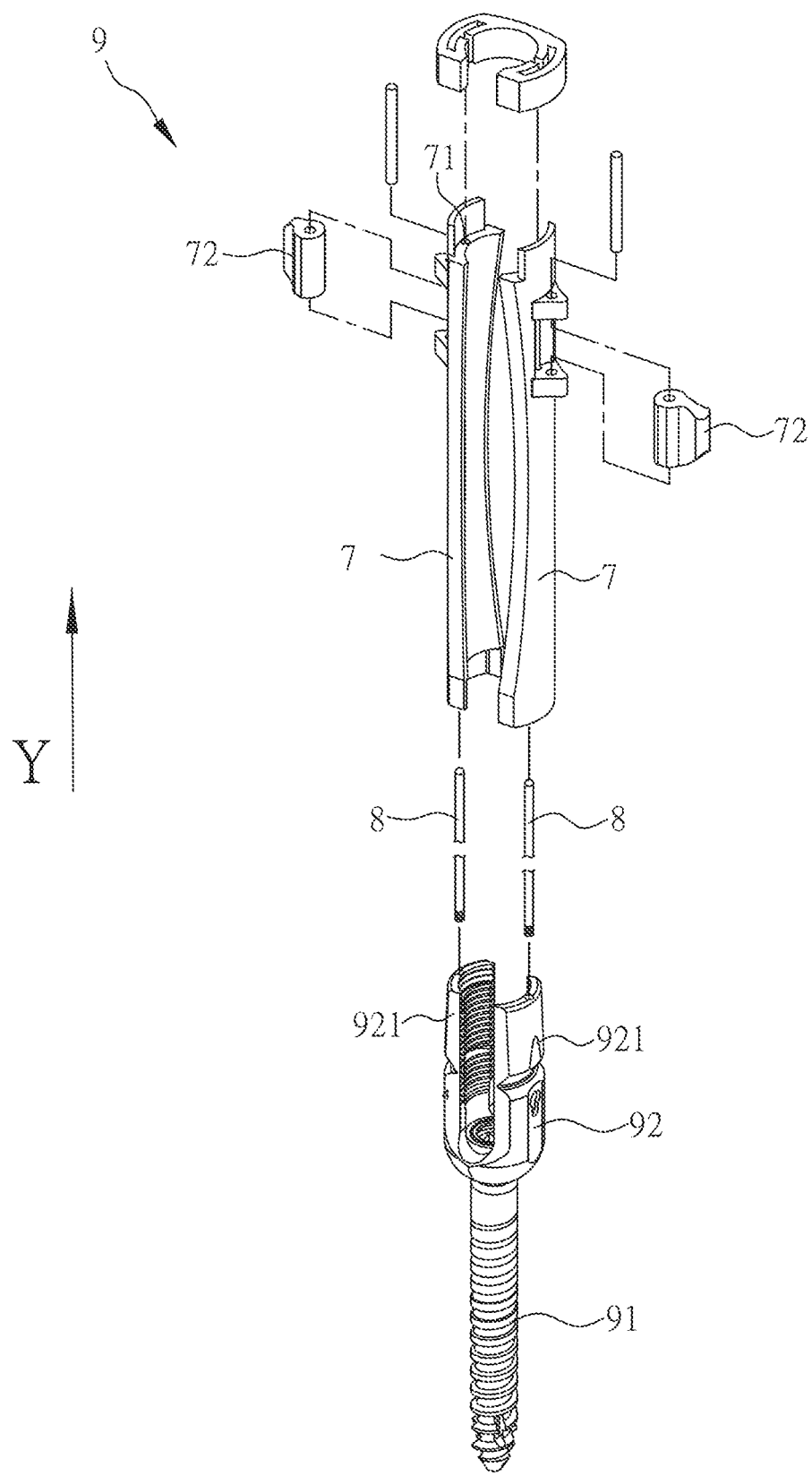
FIG. 1B illustrates an explosive view of the extending member and the pedicle screw shown in FIG. 1A.
Figure 1C:
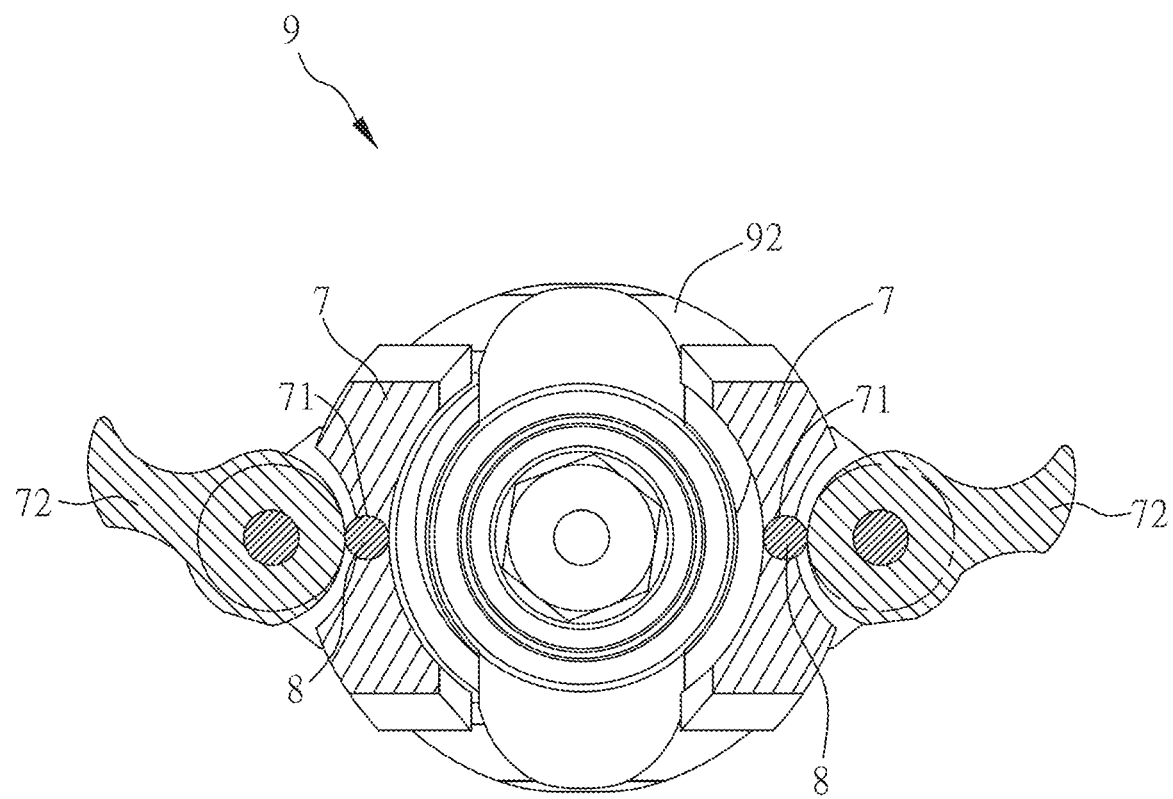
FIG. 1C illustrates a cross-sectional view taken along line A-A of FIG. 1B.
Figure 2:
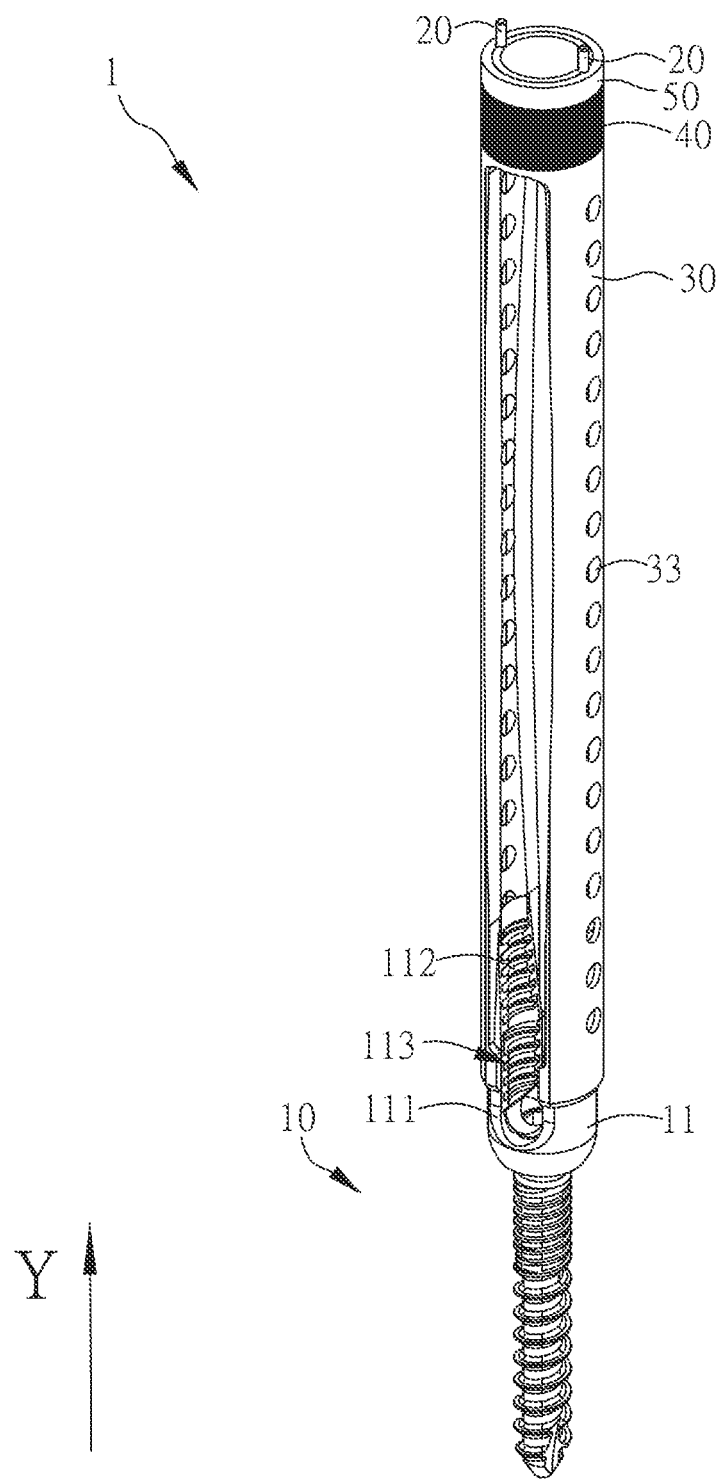
FIG. 2 illustrates a schematic view of an embodiment of a device for surgery to stabilize bone segments of the present disclosure.
Figure 3:
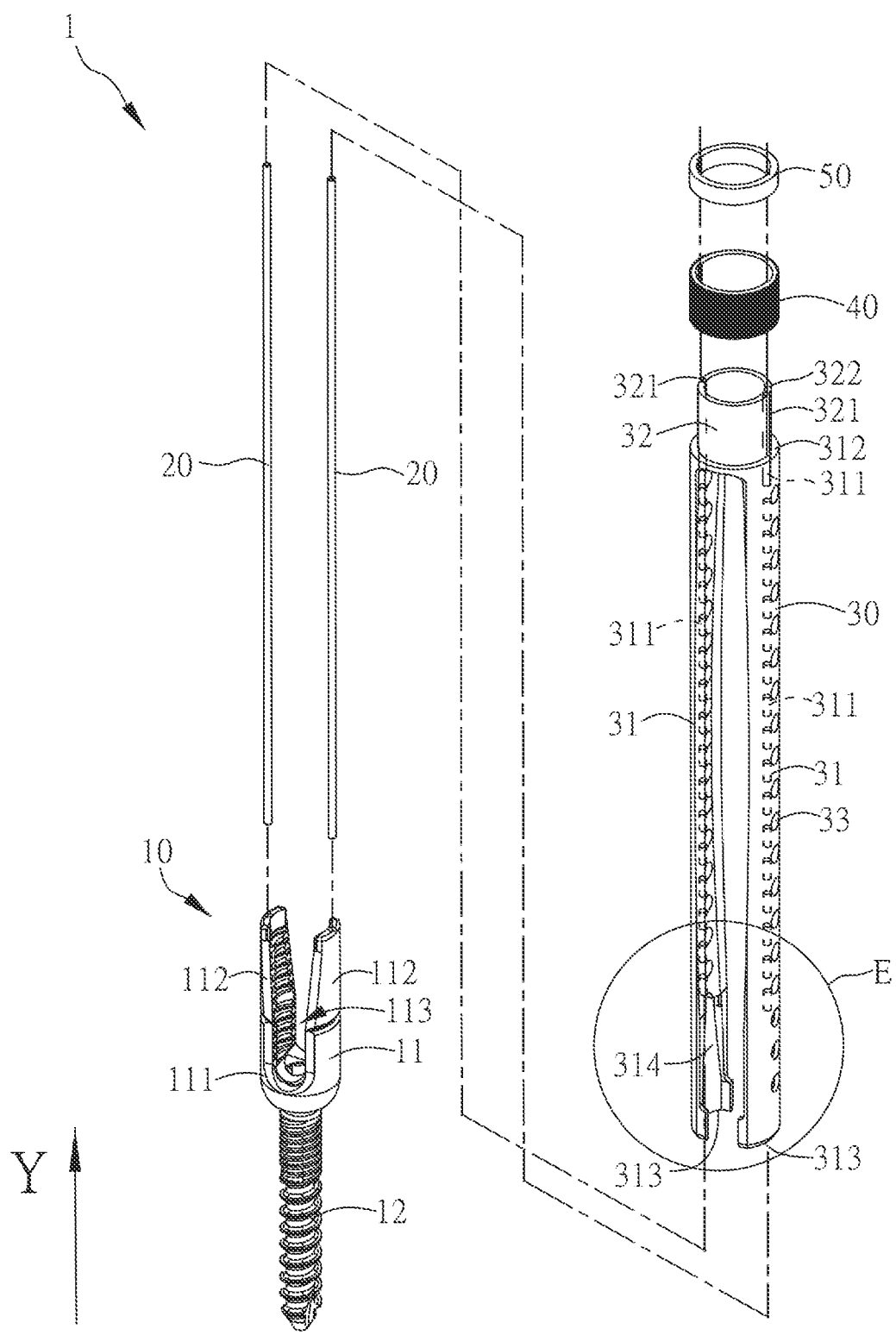
FIG. 3 illustrates an explosive view of the device for surgery to stabilize bone segments shown in FIG. 2.

FIG. 2 illustrates a schematic view of an embodiment of a device for surgery to stabilize bone segments of the present disclosure, and FIG. 3 illustrates an explosive view of the device for surgery to stabilize bone segments shown in FIG. 2; please refer to both FIG. 2 and FIG. 3. In this embodiment, a device 1 for surgery to stabilize bone segments (hereinafter referred to as device 1) comprises a screw assembly 10, at least one supporting member 20, an extending member 30, and a fastening member 40. The screw assembly 10 of the embodiment is a pedicle screw (also known as a pedicle bone screw) of the pedicle screw internal fixation system, the supporting member 20 and the extending member 30 are installed in the screw assembly 10, and the fastening member 40 is disposed on the extending member 30.

Spinal disorders occur most often in the lumbar spine, especially at the L4-L5 vertebral level, where the pedicle screw fixation system is often used. The surgeon has to create a screw channel by using an instrument such as an awl to create an entry point on the lumbar vertebrae and then bore through a pedicle to the cancellous bone of the vertebra. Then the surgeon can choose whether to expand or tap the screw channel to prepare for screw implantation. After the creation of the screw channel, the device 1 of the embodiment is assembled by the surgeon on the outside of the patient's body. For example, after the screw assembly 10 is assembled, the supporting members 20 and the extending members 30 are mounted on the screw assembly 10, and then the fastening member 40 is assembled and rotated to stabilize the relative positions of the supporting member 20 and extending member 30, and to prevent the extending member 30 from breaking loose from the screw assembly 10. After the device 1 is assembled, it is implanted on the vertebral body; that is, the screw assembly 10 with the supporting members 20 and the extending members 30 are implanted together on the vertebral body. However, in other embodiments, the surgeon may first implant the screw assembly 10 with the supporting member 20 on the vertebral body and then install the extending member 30 and the fastening member 40 along the supporting member 20.

Figure 4:
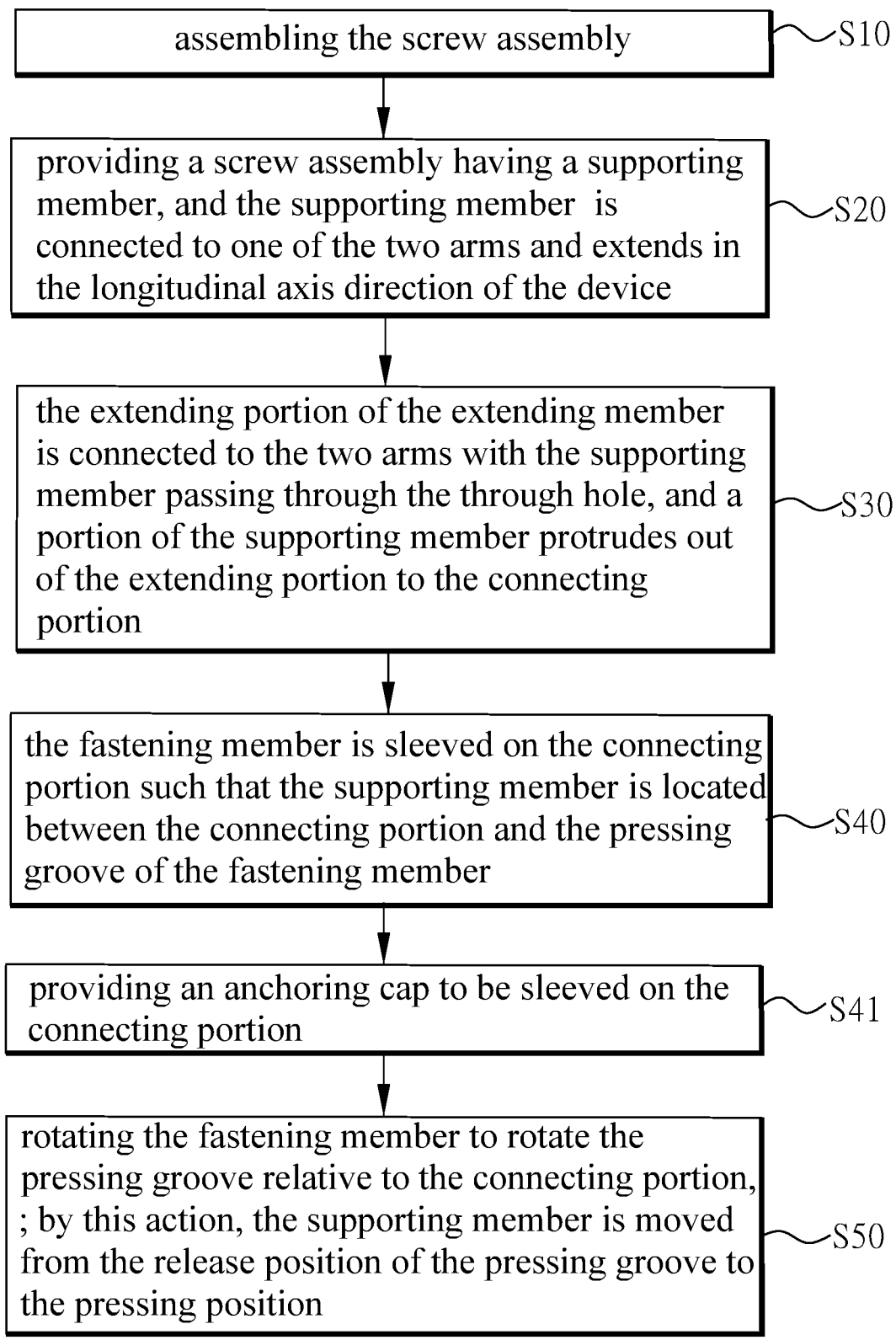
FIG. 4 illustrates a flow chart showing the steps of the assembly method of the device shown in FIG. 2.

FIG. 4 illustrates a flow chart showing the steps of the assembly method of the device shown in FIG. 2; please refer to FIG. 2, FIG. 3 and FIG. 4 at the same time. The assembly method and the assembly order of the device 1 are used below to describe the detailed structure and connection relationship of the screw assembly 10, the supporting member 20, the extending member 30, and the fastening member 40.

Step S10: assembling the screw assembly 10.

The screw assembly 10 of the present embodiment comprises a receiver 11 and an anchoring member 12, and the receiver 11 is generally formed in a U shape, so it may also be referred to as a U-shaped head. The receiver 11 has a retainer 111 and two arms 112. The retainer 111 is located in the recess of the receiver 11, and the opposite arms 112 extend in the longitudinal axis direction Y of the device 1 on both sides of the retainer 111. The retainer 111 and the arms 112 together form an accommodating space 113 for accommodating the spinal surgery accessory, such as a connecting rod of the pedicle screw internal fixator system and a fastening screw for fixing the connecting rod. In addition to accommodating the connecting rod and the fastening screw, the surgeon also uses the accommodating space 113 to connect various spinal surgical instruments with the screw assembly 10 during the operation.

The anchoring member 12 of this embodiment is a screw shaft, and the anchoring member 12 is connected to the retainer 111. The anchoring member 12 and the receiver 11 can be integrally formed or can be connected by a spherical joint. In terms of commercial products, the former is called a single-axis screw or monoaxial screw, and the latter is called a multi-axial, universal or polyaxial screw. This embodiment is an example of a polyaxial screw. The assembly method of the screw assembly 10 will be briefly described below.

The anchoring member 12 of this embodiment has a spherical head, and the retainer 111 is a through hole. The spherical head of the anchoring member 12 is accommodated in the retainer 111. During assembly of the screw assembly 10, the anchoring member 12 is first passed through the accommodating space 113 and the retainer 111; since the diameter of the spherical head of the anchoring member 12 is greater than the inner diameter of the retainer 111, the anchoring member 12 is limited in the retainer 111. Preferably, the screw assembly 10 further has an inner cap 13. The inner cap 13 is placed on the spherical head of the anchoring member 12, and then the spherical head of the anchoring member 12 and the inner cap 13 are pressed into the retainer 111 together for fixation to the retainer 111 by a jig. In addition, a thread on the anchoring member 12 can be customized depending on the location of the implantation. A pedicle screw is the one type of screw with a shaft having the same pitches evenly distributed on its body. A cortical screw is another type with a shaft having a thread formed with shorter pitches in the upper portion and longer pitches in the lower portion. However, the present disclosure is not limited to any type of the screws mentioned herein. In addition, the general definition of a minimally invasive spinal surgery is that a single surgical incision is no greater than three centimeters. According to the definition, both the pedicle screw and cortical screw can be implemented in minimally invasive spinal surgeries.

Step S20: providing a screw assembly 10 having a supporting member 20, and the supporting member 20 is connected to one of the two arms 112 and extends in the longitudinal axis direction Y of the device 1.

Figures 5A, 5B, 5C:
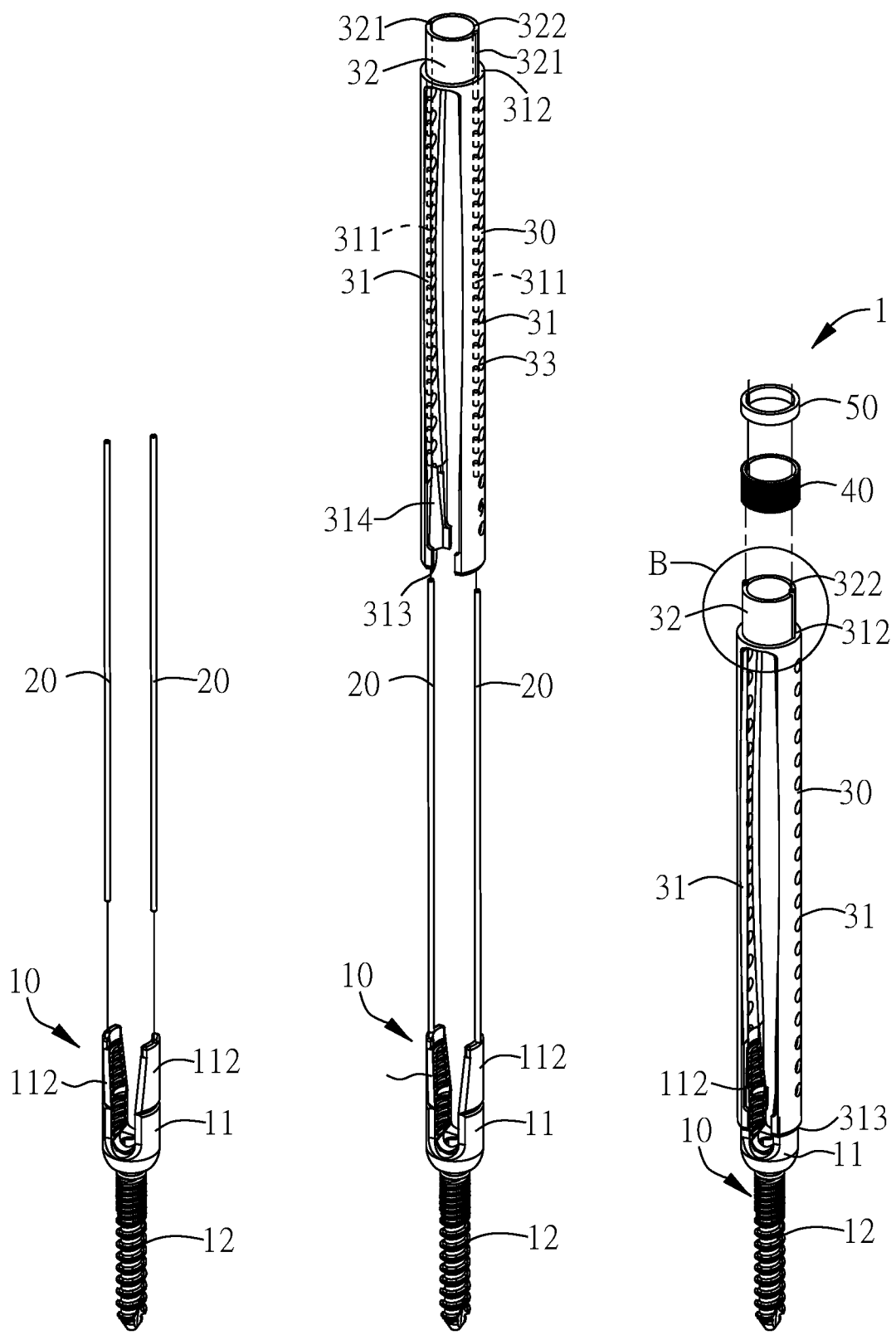
FIG. 5A illustrates a schematic view of the supporting member of FIG. 3 before being assembled with the screw assembly.
FIG. 5B illustrates a schematic view of the extending member of FIG. 3 before being assembled with the screw assembly.
FIG. 5C illustrates a schematic view of the extending member of FIG. 3 after being assembled with the screw assembly.

FIG. 5A illustrates a schematic view of the supporting member of FIG. 3 before being assembled with the screw assembly, and FIG. 5B illustrates a schematic view of the extending member of FIG. 3 before being assembled with the screw assembly; please refer to FIG. 5A. After the assembly of the screw assembly 10 is completed, at least one supporting member 20 can be connected to the top surface of one of the arms 112 of the screw assembly 10 in a top-down manner. The combined supporting member 20 and the arm 112 are also extended in the longitudinal axis direction Y. In order to achieve a better fixing effect, two supporting members 20 can be respectively connected to the top surface of the two arms 112 of the screw assembly 10.

Preferably, the supporting member 20 can be a long rod structure and can be made of various biocompatible and rigid materials, such as titanium alloy. In this embodiment, the supporting member 20 is connected to the top surface of the arms 112 in a screw-lock manner and is assembled into the screw assembly 10 having a supporting member 20. In other embodiments, other detachable connections are also possible. In other embodiments, the supporting member 20 and the receiver 11 may be integrally formed. When the screw assembly 10 (step S10) is assembled, the screw assembly having the supporting member 20 is provided.

Step S30: the extending portion 31 of the extending member 30 is connected to the two arms 112 with the supporting member 20 passing through the through hole 311, and a portion of the supporting member 20 protrudes out of the extending portion 31 to the connecting portion 32.

FIG. 5C illustrates a schematic view of the extending member of FIG. 3 after being assembled with the screw assembly; please refer to FIG. 5B and FIG. 5C. The extending member 30 comprises at least one extending portion 31 and a connecting portion 32. For enhancing the stability, the extending member 30 preferably has two extending portions 31 as described in this embodiment, but in other implementations, the extending member 30 can also be designed with an elongated cylinder or sleeve configuration as a single extending portion 31. From the direction shown in FIG. 5B, for example, the connecting portion 32 is designed to be disposed on a top surface 312 engaged with the two extending portions 31 such that the connecting portion 32 and the two extending portions 31 form an upside-down U shape. In this embodiment, the connecting portion 32 has an outer diameter of 11.6 mm, the two extending portions 31 are formed to have an outer diameter of 14 mm, and the top surface 312 formed on the extending portion 31 also has an outer diameter of 14 mm. The connecting portion 32 having a smaller outer diameter retains a space on the top surface 312 to allow the fastening member 40 to be sleeved thereon, and the outer diameter (14 mm) of the connecting portion 32 having the fastening member 40 sleeved thereon is no larger than the maximum outer diameter (14 mm) of the two extending portions 31, which simplifies the appearance of the device and avoids an increase in size.

Compared with the conventional extending member 7 and its fastening structure 72, the configuration of the fastening member 40 can provide the effects of fixing the supporting member 20 and the extending member 30, and more importantly, it can avoid increasing the maximum outer diameter of the device 1, thereby achieving the goal of minimally invasive surgery. Taking an anti-torque sleeve used in the surgery as an example, the anti-torque sleeve is used to cover the extending member 30 and then moved from top to bottom to the operating position on the screw assembly 10, but in order to pass through the fastening structure 72 of the extending member 7, the anti-torque sleeve must have a large inner diameter; that is, the size of the anti-torque sleeve itself should be increased, making the incision larger when the anti-torque sleeve passes through the incision. On the other hand, the overall outer diameter of the device 1 of the embodiment is not increased when the fastening member 40 is used, so even if the anti-torque sleeve is added, the outer diameter can still be less than or equal to three centimeters, which meets the requirement of minimally invasive surgery.

As shown in FIG. 3 and FIG. 5B, each extending portion 31 has a through hole 311, the through hole 311 has a long channel shape, the openings on both sides of the through hole 311 are respectively located at the top surface 312 and the bottom 313 of the extending portion 31, and the bottom 313 is sleeved on the arm 112. Upon assembly, the surgeon can insert the supporting member 20 into the extending portion 31 from the opening of the bottom 313. Thereafter, the extending portion 31 is moved to the arm 112 with the supporting member 20 as an axis such that the two supporting members 20 pass through the through holes 311 of the extending portions 31 respectively and protrude out of the opening of the top surfaces 312 to the side of the connecting portions 32. The bottom 313 of the extending portion 31 has a configuration corresponding to that of the arm 112, and the configuration is for connection to the arm 112. As shown in FIG. 5C, the extending portion 31 of the present embodiment has the same curved surface structure as the arm 112 and is connected to the top of the arm 112 when the extending portion 31 passes through the supporting member 20.

Preferably, the extending portion 31 of this embodiment is connected to the arm 112 by a recess 314 formed by the bottom 313. In detail, the bottom of each extending portion 31 has a recess 314, and the opening of the through hole 311 at the bottom 313 is disposed in the recess 314 (refer to FIG. 13). The recess 314 is externally connected to the bottom 313 of the extending portion 31 and to a side connected to the bottom 313. In other words, the recess 314 has two sides which are open and can be externally connected; one of them is the bottom surface of the extending portion 31, and the other is the side opposite the other extending portion 31, such that the recess 314 can be abutted on the outer side of the arm 112 to connect the extending portion 31 with the arm 112. It should be noted that in the case where the size of the mechanism is reduced and the connection is simplified, the reason why the extending portion 31 will not be easily detached from the arm 112 is that the extended portion 31 is subjected to the pressing of the inner supporting member 20.

Figure 6:
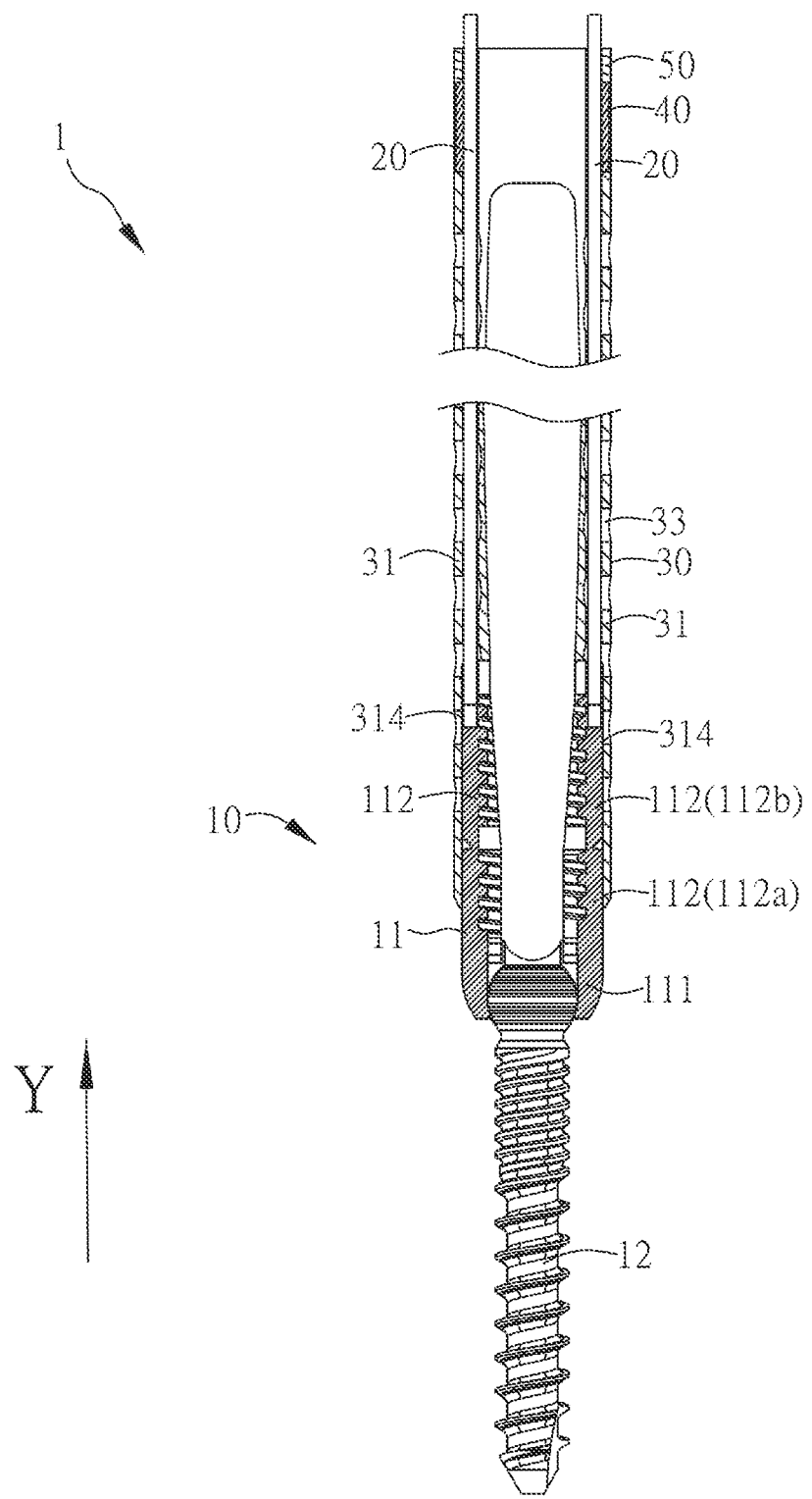
FIG. 6 illustrates a cross-sectional view of the device shown in FIG. 2.

Now refer to FIG. 6, which is a cross-sectional view of the device shown in FIG. 2. The arm 112 of the receiver 11 has a joint 112a and a removable portion 112b. The joint 112a is located on two sides of the retainer 111 and is connected to the retainer 111, and the removable portion 112b is connected to the joint 112a in the longitudinal axis direction Y. After the screw assembly 10 is implanted into the vertebral body of the patient, the surgeon can remove the removable portion 112b using a breaker. Preferably, the recess 314 of this embodiment has a depth greater than the length of the removable portion 112b such that the recess 314 is simultaneously engaged with the removable portion 112b and the joint portion 112a. Since it is difficult to avoid the removable portion 112b being broken accidentally due to improper application of force during surgery, the design of the recess 314 having a relatively long depth can prevent the extending member 30 from breaking off.

The connecting portion 32 is located at the other end of the extending member 30 opposite the screw assembly 10. After the supporting member 20 passes through the through hole 311 of the extending portion 31, the supporting member 20 will protrude out of the opening of the top surface 312 to the connecting portion 32.

Figure 7:
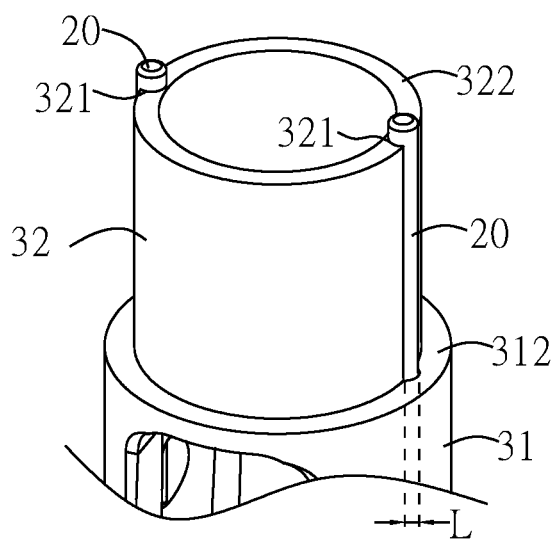
FIG. 7 illustrates an enlarged view of a region B shown in FIG. 5C.

Please refer to FIG. 7, which is an enlarged view of area B shown in FIG. 5C. In this embodiment, the length of the supporting member 20 is not limited, but the length of the supporting member 20 should be able to allow the supporting member 20 to protrude out of the top surface 312 and to reach the outside of the connecting portion 32 after passing through the through hole 311. Preferably, the length of the supporting member 20 may have a length of between 117 mm and 121 mm and a diameter of about 2 mm or less, preferably 1.2 mm. Preferably, the supporting member 20 can protrude out of the connecting portion 32 along the longitudinal axis direction Y. For example, the supporting member 20 protrudes out of the top surface 322 of the connecting portion 32 by 1 mm to 3 mm, which can be used to identify the depth at which the supporting member 20 is screwed to the arm 112. For example, suppose that in a normal case, the supporting member 20 protrudes out of the top surface 322 of the connecting portion 32 by 2 mm; when the supporting member 20 is screwed to the arm 112 and the extending member 30 passes through the through hole 311, the height of the supporting member 20 protruding out of the connecting portion 32 will be greater than 2 mm, indicating that the supporting member 20 is not securely connected to the arm 112. At this time, additional force can be applied again to press the supporting member 20 downwardly to go further into the arm 112.

The connecting portion 32 preferably has at least one limiting groove 321. As shown in FIG. 3 and FIG. 7, the connecting portion 32 of this embodiment has two opposite limiting grooves 321 for being in communication with the through holes 311 of the two extending portions 31, respectively. The configuration of the limiting groove 321 corresponds with that of the supporting member 20. In this embodiment, the supporting member 20 is cylindrical, so the limiting groove 321 is designed as an arc-shaped recess. After the supporting member 20 passes through the through hole 311, a portion of the supporting member 20 protruding out of the top surface 312 is accommodated in the limiting groove 321. Since the limiting groove 321 is an arc-shaped recess, the supporting member 20 is partially covered in the limiting groove 321. That is, one side of the supporting member 20 is located in the limiting groove 321 and the other side is exposed outside the limiting groove 321. Furthermore, the length of the supporting member 20 that protrudes out of the surface of the connecting portion 32 is referred to as a predetermined length L; that is, the supporting member 20 protrudes out of the surface of the connecting portion 32 by a predetermined length L, as shown in FIG. 7 (please also refer to FIG. 9). The predetermined length L may preferably be between 2 mm and 4 mm.

Step S40: The fastening member 40 is sleeved on the connecting portion 32 such that the supporting member 20 is located between the connecting portion 32 and the pressing groove 41 of the fastening member 40.

Figure 8:
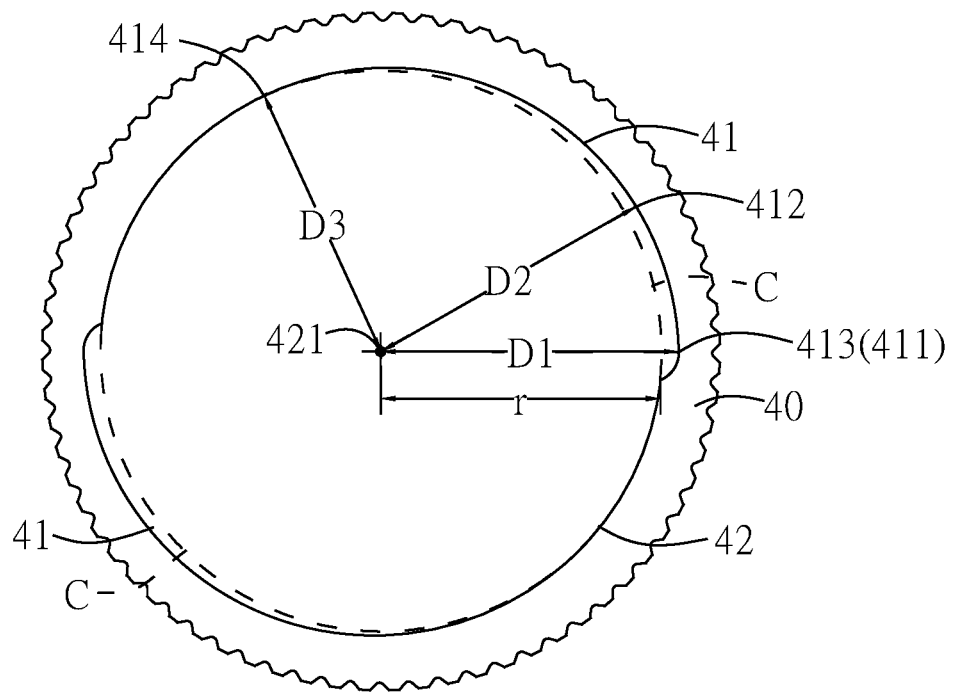
FIG. 8 illustrates an enlarged view of the fastening member shown in FIG. 5C.
Figure 9:
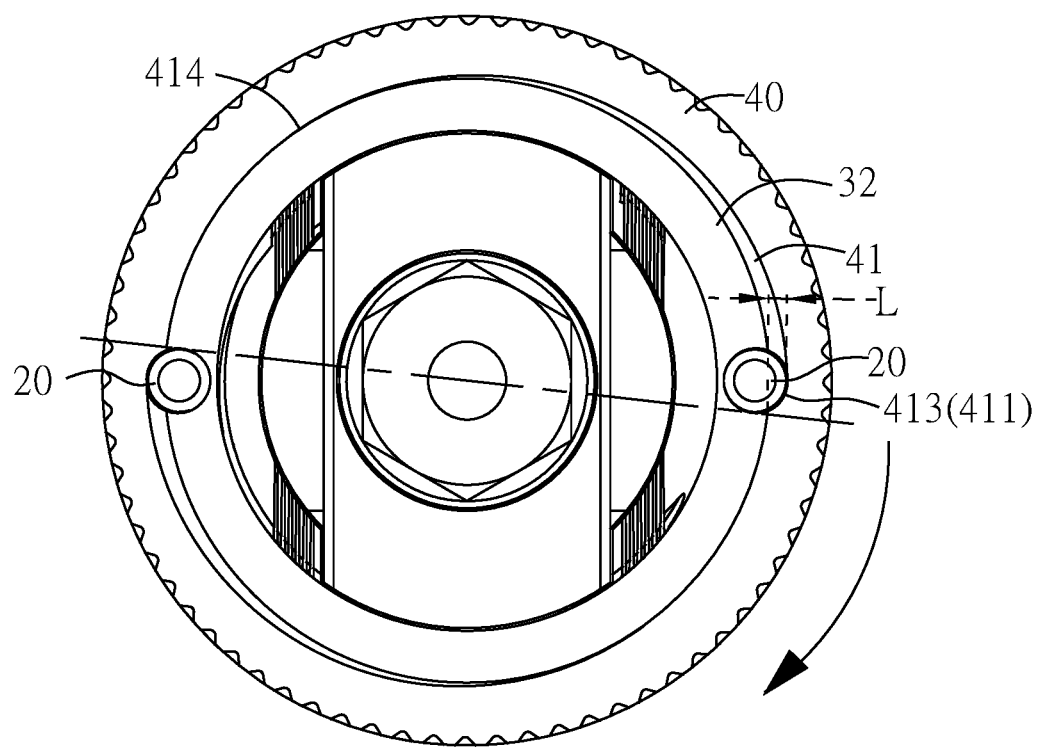
FIG. 9 illustrates a top view of the fastening member shown in FIG. 5C after being assembled with the connecting portion.

FIG. 8 illustrates an enlarged view of the fastening member shown in FIG. 5C, and FIG. 9 illustrates a top view of the fastening member shown in FIG. 5C after being assembled with the connecting portion; please refer to both FIG. 8 and FIG. 9. After the extending member 30 is assembled with the screw assembly 10, the surgeon can set the fastening member 40 to be sleeved on the connecting portion 32 of the extending member 30. The inner side of the fastening member 40 has at least one pressing groove 41. The fastening member 40 of this embodiment has two pressing grooves 41 symmetrically disposed to correspond to the supporting members 20 on the two opposite sides of the connecting portions 32. The surgeon can first align the release position 411 of the pressing groove 41 with the supporting member 20 and then set the fastening member 40 to be sleeved on the connecting portion 32. After the assembly, the supporting member 20 is located between the connecting portion 32 and the pressing groove 41. Details of the release position 411 will be further described later.

The connecting portion 32 of the extending member 30 of this embodiment is substantially cylindrical (the central opening is for the surgical instrument to enter and exit), and the fastening member 40 is ring-shaped and has a round opening round 42. The inner diameter of the round opening 42 is slightly larger than or substantially equal to the outer diameter of the connecting portion 32 such that the fastening member 40 can be sleeved on the connecting portion 32 through the round opening 42. The pressing groove 41 is also formed on the inner side of the fastening member 40, and the round opening 42 is in communication with the pressing groove 41. As shown in FIG. 8, the pressing groove 41 is an arc-shaped recess that expands outward based on the round opening 42. Specifically, there is a reference arc C disposed between the pressing groove 41 and the round opening 42, and the pressing groove 41 is expanded from the reference arc C to the outside of the fastening member 40. It should be noted that the reference arc C is a virtual reference line which is located at the boundary between the pressing groove 41 and the round opening 42.

Figure 11:
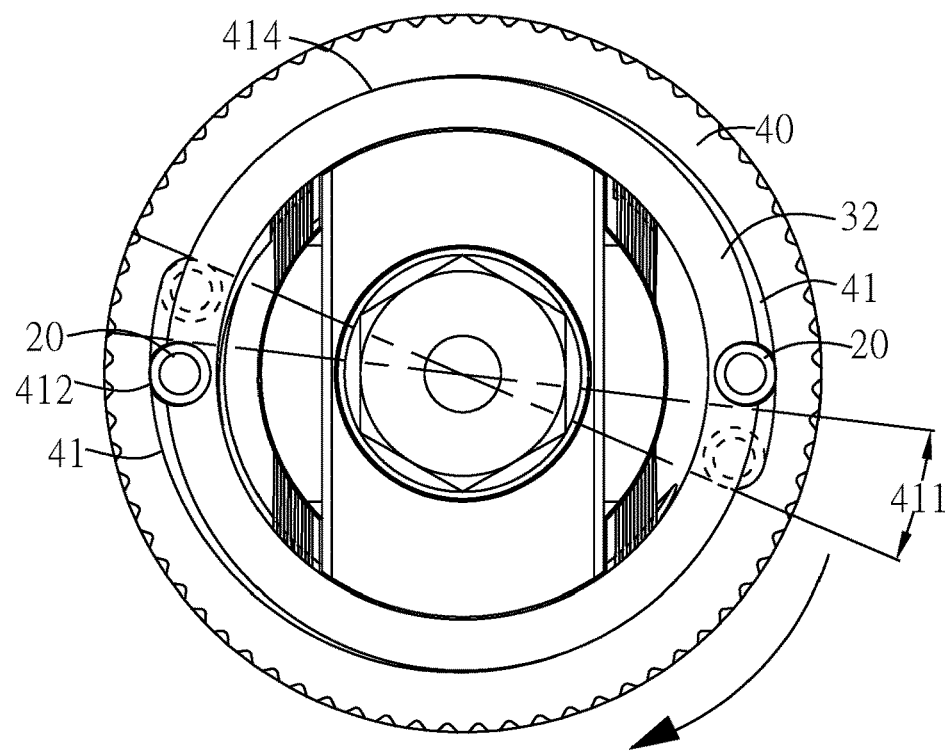
FIG. 11 illustrates a schematic view of the supporting member shown in FIG. 9 moving in the segment of a release position.

In this embodiment, the pressing groove 41 comprises a release position 411 of the supporting member 20 (shown in FIG. 9) and a pressing position 412 (please refer to FIG. 11). Also, the round opening 42 has a center point 421. The release position 411 may be, for example, (1) a position where the supporting member 20 has not been pressed, or has not been interfered with by the connecting portion 32; or (2) when the supporting member 20 is in this position, a frictional force or interference strength sufficient to prevent the extending member 30 from moving relative to the supporting member 20 is not formed between the supporting member 20 and the connecting portion 32. From the operation angle, when the supporting member 20 is in the release position 411 of the pressing groove 41, the surgeon can pull the extending member 30 upward along the longitudinal axis direction Y and out of the supporting member 20. Conversely, the pressing position 412 is, for example, a position where (1) the supporting member 20 is pressed by the fastening member 40 or is interfered with by the connecting portion 32; or (2) when the supporting member 20 is in this position, there is a frictional force or interference strength between the supporting member 20 and the connecting portion 32 that prevents the extending member 30 from moving relative to the supporting member 20. At this time, the surgeon cannot pull the extending member 30 upward in the longitudinal axis direction Y and out of the supporting member 20, and the extending member 30 is not affected by the external force and is not separated from the screw assembly 10. In particular, the release position 411 and the pressing position 412 are determined according to the above definition and are not necessarily at any position in the pressing groove 41. For example, when working with different sizes or supporting members 20 made of different materials, the specific position of the release position 411 and the pressing position 412 on the pressing groove 41 may vary.

Referring to FIG. 8, the distance D1 between the release position 411 and the center point 421 is greater than or equal to the sum of the radius r of the round opening 42, and the predetermined length L and is greater than the distance D2 between the pressing position 412 and the center point 421.

When designing the configuration of the pressing groove 41, the distribution range of the pressing groove 41 with respect to the fastening member 40 can be defined first, which can be achieved by determining the arc length of the reference arc C. For example, a ratio of the arc length of the reference arc C to a circumference of the round opening 42 is between ⅙ and ⅖, preferably ⅜. Taking ⅜ as an example, the fastening member 40 has two symmetric pressing grooves 41 corresponding to two reference arcs C, and the arc length of each reference arc C is ⅜ of the circumference of the round opening 42, so the arc length of the two reference arcs C is ¾ of the circumference of the round opening 42. Therefore, ¼ of the inner side of the fastening member 40 abuts against the connecting portion 32, and the remaining portion extends outward to form two symmetric pressing grooves 41.

The pressing groove 41 is a recess which is laterally disposed inside the fastening member 40, and the groove space gradually decreases from one end to the other end. Specifically, the starting point 413 of the pressing groove 41 (which may be one of the release positions 411 of the supporting member 20) is the position defined by pushing out one end of the reference arc C to the outside of the fastening member 40 for the predetermined length L. The end point 414 of the pressing groove 41 (which may be one of the pressing positions 412 of the supporting member 20) overlaps with the other end of the reference arc C. In addition, the distance from the center point 421 is shown as the distance, and the starting point 413 of the pressing groove 41 is the position having the maximum distance between the inner side of the fastening member 40 and the center point 421 (that is, the distance D1 shown in FIG. 8). The maximum distance is greater than the sum of the radius r of the round opening 42 and the predetermined length L. The distance D3 between the end point 414 of the pressing groove 41 and the center point 421 is substantially equal to the radius r of the round opening 42; that is, the inner side of the fastening member 40 has the minimum distance to the center point 421 (the distance D3 shown in FIG. 8). Therefore, the distance between the pressing groove 41 and the center point 421 gradually decreases from the starting point 413 to the end point 414, thereby forming a tapered recess.

Figure 10:
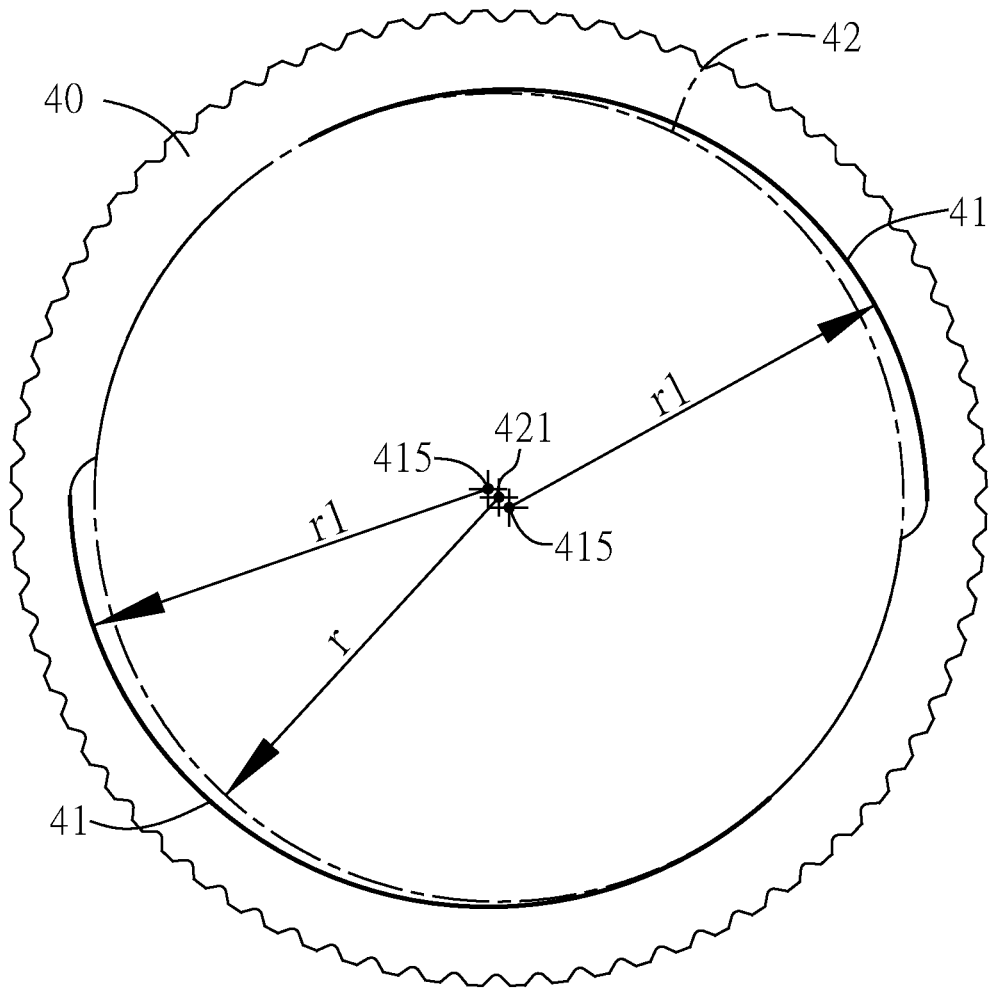
FIG. 10 illustrates an enlarged view of the fastening member shown in FIG. 8.

FIG. 10 is an enlarged view of the fastening member shown in FIG. 8. Referring to FIG. 10, the way to design a round opening 42 and a pressing groove 41 inside the fastening member 40 is described below. First, a round opening 42 is defined inside the fastening member 40, which is shown in the figure. The radius r of the round opening 42 of this embodiment is 5.8 mm. Next, the center point 421 taken from the round opening 42 is shifted to the right by 1.3 mm and downward by 1.5 mm as the center point 415 of one of the pressing grooves 41, and a ⅜ circle having a radius r1 of 6 mm is drawn, which is the line segment representing the arc of the pressing groove 41 of the first quadrant. Thereafter, the center point 421 of the round opening 42 is shifted to the left by 1.3 mm and upward by 1.5 mm, as the center point 415 of another pressing groove 41, and a ⅜ circle having a radius r1 of 6 mm is also drawn, which is a line segment representing the arc of the pressing groove 41 of the third quadrant. The contour of the line segment representing the pressing groove 41 overlapping the round opening 42 is cut by a processing tool to form the inner configuration of the fastening member 40.

In step S40, when the fastening member 40 is sleeved on the connecting portion 32, the release position 411 is aligned with the supporting member 20, and then the fastening member 40 is set to be sleeved on the connecting portion 32. At this time, the supporting member 20 is located between the connecting portion 32 and the release position 411 of the pressing groove 41, as shown in FIG. 9. Since the fastening member 40 is assembled with the extending member 30 in a manner similar to that with the connecting portion 32, the device 1 has a relatively simplified appearance and the maximum width is not increased compared to the prior art design.

Step S41: providing an anchoring cap 50 to be sleeved on the connecting portion 32.

Preferably, the device 1 of this embodiment further comprises an anchoring cap 50. First, the fastening member 40 is sleeved on the connecting portion 32 (step S40), and then the anchoring cap 50 is sleeved on the connecting portion 32 (step S41). After assembly, the anchoring cap 50 is located at the top of the extending member 30 to limit the fastening member 40 between the extending portion 31 and the anchoring cap 50, thereby preventing the fastening member 40 from falling off the top of the extending member 30.

Step S50: rotating the fastening member 40 to rotate the pressing groove 41 relative to the connecting portion 32; by this action, the supporting member 20 is moved from the release position 411 of the pressing groove 41 to the pressing position 412.

Figure 12:
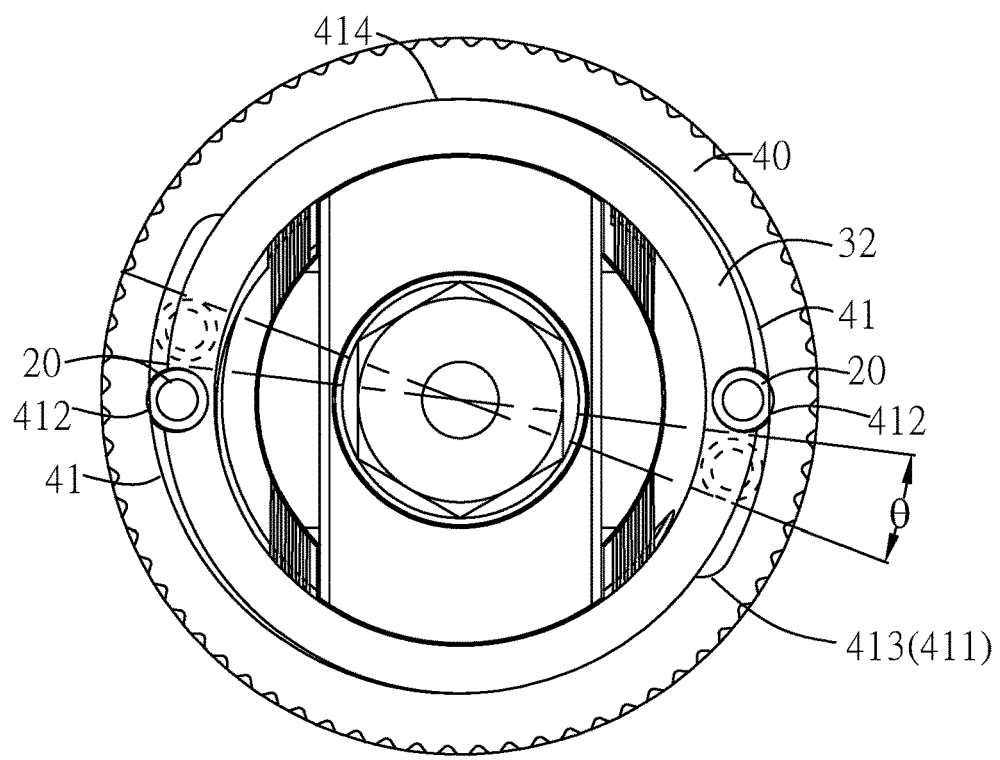
FIG. 12 illustrates a schematic view of the supporting member shown in FIG. 11 moving from the release position to a pressing position of the pressing groove.

FIG. 11 illustrates a schematic view of the supporting member shown in FIG. 9 moving in the segment of the release position, and FIG. 12 illustrates a schematic view of the supporting member shown in FIG. 11 moving from the release position to the pressing position of the pressing groove. After the fastening member 40 is sleeved on the outside of the connecting portion 32 (step S40), the surgeon can turn the fastening member 40 to cause the fastening member 40 to rotate relative to the connecting portion 32. As shown in FIG. 9, FIG. 11 and FIG. 12, when the fastening member 40 is rotated in a clockwise direction relative to the connecting portion 32, the supporting member 20 moves relative to the fastening member 40 along the pressing groove 41 from the release position 411 to the pressing position 412.

In detail, in this embodiment, when the fastening member 40 is rotated by 0 to 16 degrees in the clockwise direction, the supporting member 20 is uncompressed or not squeezed and is in a release state, so the release position 411 may be any position in the segment, as shown in FIG. 11. Moreover, since the pressing groove 41 is a tapered recess, when the pressing groove 41 presses the supporting member 20 inwardly, the interference between the supporting member 20 and the connecting portion 32 will gradually increase with the angle of rotation until the fastening member 40 cannot be rotated any further. At this time, this position can be referred to as the pressing position 412. Therefore, in this embodiment, the release position 411 is not adjacent to the pressing position 412. In this embodiment, when the fastening member 40 is rotated by more than 30 degrees, the pressing groove 41 presses the supporting member 20 to the interference intensity at which the extending member 30 cannot move relative to the supporting member 20. As shown in FIG. 12, an angle θ between the line connecting the pressing position 412 and the center point 421 and the line connecting the release position 411 and the center point 421 can be greater than 14 degrees.

When the supporting member 20 is gradually approaching the pressing position 412 or even reaches the pressing position 412, the pressing groove 41 provides an inwardly pressing force to the supporting member 20 for pushing the supporting member 20 to move inwardly; as a result, the supporting member 20 and the connecting portion 32 are pressed to be fixed with respect to each other, thereby providing the effect of fixing the relative positions of the supporting member 20 and the extending member 30. At this time, the supporting member 20 cannot move relative to the extending member 30 in the longitudinal axis direction Y, and the extending member 30 is prevented from breaking loose from the arm 112. Specifically, when the supporting member 20 is in the pressing position 412, the supporting member 20 generates a force on the connecting portion 32, and the connecting portion 32 generates a counter force on the supporting member 20. If the extending member 30 is to be moved relative to the supporting member 20, the maximum static friction between the force and the counter force must be overcome. Therefore, as the rotational amplitude increases, the maximum static friction between the force and the counter force increases, thereby making it more difficult for the extending member 30 to move with respect to the supporting member 20.

It should be noted that the pressing position 412 of the pressing groove 41 of the present embodiment is not necessarily the same as the end point 414 and is preferably not the same. Between the pressing position 412 and the end point 414, the distance between the pressing groove 41 and the center point 421 is still gradually reduced, and the groove space is continuously reduced, thereby offsetting the wear and tear caused by the use of the supporting member 20 and maintaining the original function. In detail, after the supporting member 20 is operated for a long time or a plurality of times, the supporting member 20 will wear out and become thinner. At this time, as long as the angle of the rotation of the fastening member 40 is increased when fastening, the supporting member 20 will move further along the pressing groove 41 toward the end point 414, thereby solving the problem that the supporting member 20 is not easily tightened due to wear and tear. Of course, the pressing position 412 of the supporting member 20 will now be closer to the end point 414. It can also be seen that the pressing position 412 is not a fixed position but can be changed according to real requirements.

In general, the surgeon first screws the supporting member 20 to the arm 112 of the receiver 11, as shown in FIG. 5A and FIG. 5B. Then the extending member 30 is passed through the supporting member 20 via the through hole 311 of the extending portion 31, and the recess 314 is engaged with the arm 112 of the receiver 11, as shown in FIG. 5C, and the supporting member 20 and the connecting portion 32 can be tightened by rotating the fastening member 40, as shown in FIG. 11 and FIG. 12. The aforementioned assembly procedure is simple, and after the installation is completed, the surgeon can implant the device 1 into the vertebral body of the patient by using the instrument, and the device 1 can be used together with other surgical instruments. The fastening member 40 is sleeved on the connecting portion 32, and the supporting member 20 is located between the connecting portion 32 and the pressing groove 41, so the fastening member 40 does not add any additional outer diameter to the device 1, nor does the extending member 30, and the action of rotating the fastening member 40 is convenient to perform.

When removing the extending member 30, the surgeon only needs to reversely rotate the fastening member 40 to move the supporting member 20 from the pressing position 412 of the pressing groove 41 toward the release position 411. At this time, the pressure between the supporting member 20 and the connecting portion 32 is gradually released, so the extending member 30 can be removed along the longitudinal axis direction Y.

Figure 13:
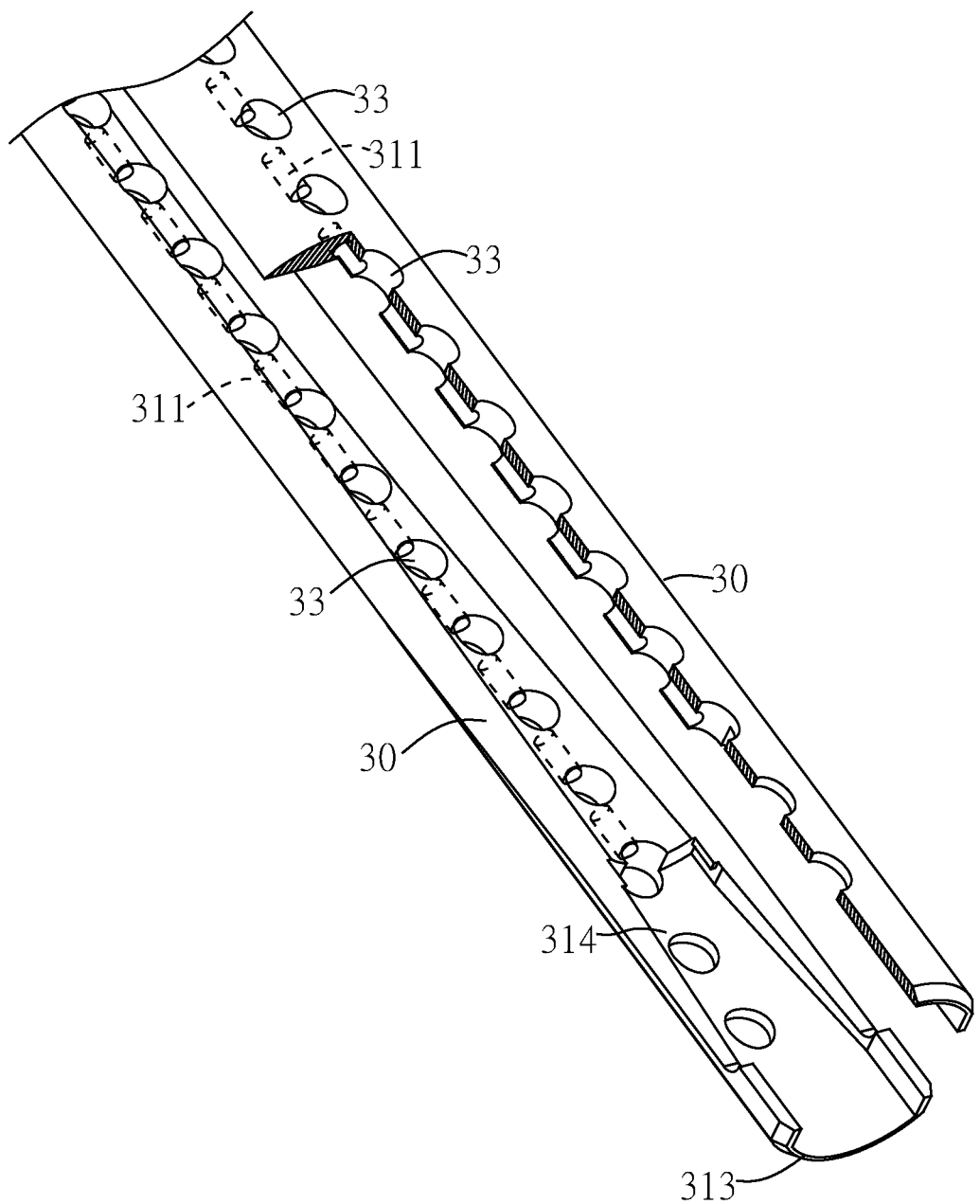
FIG. 13 illustrates an enlarged view of area E shown in FIG. 3.

The extending member 30 of this embodiment can be reused, but it must be disinfected before subsequent use. The extending member 30 has a plurality of side through holes 33 which are arranged in parallel with each other in the extending portion 31 and are in communication with the through hole 311, as shown in FIG. 13, which is an enlarged view of area E shown in FIG. 3. By the arrangement of the side through holes 33, when sterilization is being performed, the vapor can enter the through hole 311 via the side through holes 33 to prevent the accumulation of blood in the through hole 311.

In addition, the present disclosure further provides an extending assembly for use in a device for surgery to stabilize bone segments. The device comprises a screw assembly and at least one supporting member. The screw assembly comprises a receiver. The receiver has a retainer and two opposite arms, and two supporting members are respectively connected to one of the two arms. For the detailed structure of the screw assembly and the supporting member and the connection relationship thereof, please refer to the screw assembly 10 and the supporting member 20 of the foregoing embodiment, and no further details are provided herein. Furthermore, the extending assembly comprises an extending member and a fastening member. The extending member comprises a connecting portion and at least one extending portion, wherein the extending portion is connected to the two arms with the supporting member passing through the through hole, and a portion of the supporting member protrudes out of the extending portion to the connecting portion. The fastening member is sleeved on the connecting portion, and the fastening member has at least one pressing groove, wherein the supporting member is located between the connecting portion and the pressing groove. Furthermore, the extending assembly further comprises an anchoring cap sleeved on the connecting portion. For the extending member and the fastening member of the extending assembly, please refer to the extending member 30 and fastening member 40 of the device 1 of the foregoing embodiment, and for the anchoring cap of the of the extending assembly, please refer to the anchoring cap 50 of the foregoing embodiment, and details are not described herein.

In addition, the present disclosure further provides a fastening member for use in a device, the device comprising at least one supporting member and an extending member. The extending member comprises a connecting portion and at least one extending portion. The extending portion has a through hole and passes through the supporting member via the through hole, and a portion of the supporting member protrudes out of the extending portion to the connecting portion. The fastening member is sleeved on the connecting portion, and the fastening member comprises at least one pressing groove, wherein the supporting member is located between the connecting portion and the pressing groove. Similarly, the fastening member may also directly refer to the fastening member 40 of the device 1 of the foregoing embodiment, and details are not described herein.

According to the present disclosure of the device for surgery to stabilize bone segments, the extending assembly, the fastening member and the assembly method thereof, when the fastening member is rotated relative to the connecting portion, the supporting member moves relative to the fastening member along the pressing groove between the release position and the pressing position. When the supporting member moves to the pressing position, the pressing groove gradually increases the pressure on the supporting member such that the resistance between the supporting member and the extending member is gradually increased, and the effect of the fixing is improved. Preferably, the relative displacement between the supporting member and the extending member is less likely to occur, so the extending member is not separated from the screw assembly.

Furthermore, since the mechanism design of the fastening member is rotatably sleeved on the connecting portion of the connecting portion, the outer diameter of the device will not be increased or will be increased slightly, which is beneficial to minimally invasive surgeries.

It should be noted that the described embodiments are only for illustrative and exemplary purposes, and that various changes and modifications may be made to the described embodiments without departing from the scope of the disclosure as disposed by the appended claims.

What is claimed is:

1. A device for surgery to stabilize bone segments comprising:
   a screw assembly comprising:
      a receiver having a retainer and two opposite arms; and
      an anchoring member connecting to the retainer;
   at least one supporting member connecting to one of the arms and extending in a longitudinal axis direction of the device;
   an extending member comprising:
      a connecting portion located at one end of the extending member opposite to the receiver; and
      at least one extending portion having a through hole, wherein the extending portion is connected to the two arms with the supporting member passing through the through hole, and a portion of the supporting member protrudes out of the extending portion to the connecting portion; and
      a fastening member sleeved on the connecting portion, the fastening member having at least one pressing groove, wherein the supporting member is located between the connecting portion and the pressing groove, and the pressing groove comprises a release position and a pressing position for the supporting member such that when the fastening member is rotated relative to the connecting portion, the supporting member moves relative to the fastening member and moves along the pressing groove between the release position and the pressing position, wherein when the supporting member is gradually approaching the pressing position, the pressing groove provides an inwardly pressing force to the supporting member for pushing the supporting member to move inwardly, so that the supporting member and the connecting portion are pressed to be fixed with respect to each other.

2. The device for surgery to stabilize bone segments as claimed in claim 1, wherein the fastening member is ring-shaped and has a round opening, the round opening is in communication with the pressing groove, and the fastening member is sleeved on the connecting portion through the round opening.

3. The device for surgery to stabilize bone segments as claimed in claim 2, wherein the round opening has a center point, and a distance between the release position and the center point is greater than a distance between the pressing position and the center point.

4. The device for surgery to stabilize bone segments as claimed in claim 3, wherein an angle between a line connecting the pressing position and the center point and a line connecting the release position and the center point is greater than 14 degrees.

5. The device for surgery to stabilize bone segments as claimed in claim 3, wherein the pressing groove has a starting point and an end point, the starting point and the end point are respectively located at opposite ends of the pressing groove, the starting point is at a position having a maximum distance between an inner side of the fastening member and the center point, and the end point is at a position having a minimum distance between the inner side of the fastening member and the center point.

6. The device for surgery to stabilize bone segments as claimed in claim 5, wherein the supporting member protrudes a predetermined length from a surface of the connecting portion, the predetermined length is set such that a maximum distance is greater than a sum of a radius of the round opening and the predetermined length, and a minimum distance is substantially equal to the radius of the round opening.

7. The device for surgery to stabilize bone segments as claimed in claim 5, wherein the pressing groove is formed on the inner side of the fastening member, and a distance between the pressing groove and the center point gradually decreases from the starting point to the end point.

8. The device for surgery to stabilize bone segments as claimed in claim 2, wherein a reference arc is defined between the pressing groove and the round opening, and a ratio of an arc length of the reference arc to a circumference of the round opening is between ⅙ and ⅖.

9. The device for surgery to stabilize bone segments as claimed in claim 1, wherein the connecting portion further comprises at least one limiting groove being in communication with the through hole of the extending portion, and the supporting member is partially covered in the limiting groove.

10. The device for surgery to stabilize bone segments as claimed in claim 1, wherein the extending member has a plurality of side through holes, and the plurality of side through holes is arranged mutually parallel to each other at the extending portion and is in communication with the through hole.

11. An extending assembly for use in a device for surgery to stabilize bone segments, the device comprising a screw assembly and at least one supporting member, the screw assembly comprising a receiver, the receiver having a retainer and two opposite arms, the supporting member being connected to one of the two arms and extending in a longitudinal axis direction of the device, the extending assembly comprising:

an extending member comprising:
  a connecting portion located at one end of the extending member opposite to the receiver; and
  at least one extending portion having a through hole, wherein the extending portion is connected to the two arms with the supporting member passing through the through hole, and a portion of the supporting member protrudes out of the extending portion to the connecting portion; and a fastening member sleeved on the connecting portion, the fastening member having at least one pressing groove, wherein the supporting member is located between the connecting portion and the pressing groove, and the pressing groove comprises a release position and a pressing position for the supporting member, such that when the fastening member is rotated relative to the connecting portion, the supporting member moves relative to the fastening member and moves along the pressing groove between the release position and the pressing position, wherein when the supporting member is gradually approaching the pressing position, the pressing groove provides an inwardly pressing force to the supporting member for pushing the supporting member to move inwardly, so that the supporting member and the connecting portion are pressed to be fixed with respect to each other.

12. The extending assembly as claimed in claim 11, wherein the fastening member is ring-shaped and has a round opening, the round opening is in communication with the pressing groove, and the fastening member is sleeved on the connecting portion through the round opening.

13. The extending assembly as claimed in claim 12, wherein the round opening has a center point, and a distance between the release position and the center point is greater than a distance between the pressing position and the center point.

14. The extending assembly as claimed in claim 13, wherein an angle between a line connecting the pressing position and the center point and a line connecting the release position and the center point is greater than 14 degrees.

15. The extending assembly as claimed in claim 13, wherein the pressing groove has a starting point and an end point, the starting point and the end point are respectively located at opposite ends of the pressing groove, the starting point is at a position having a maximum distance between an inner side of the fastening member and the center point, and the end point is at a position having a minimum distance between the inner side of the fastening member and the center point.

16. The extending assembly as claimed in claim 15, wherein the supporting member protrudes a predetermined length from a surface of the connecting portion, the predetermined length is set such that a maximum distance is greater than a sum of a radius of the round opening and the predetermined length, and a minimum distance is substantially equal to the radius of the round opening.

17. The extending assembly as claimed in claim 15, wherein the pressing groove is formed on the inner side of the fastening member and a distance between the pressing groove and the center point gradually decreases from the starting point to the end point.

18. The extending assembly as claimed in claim 12, wherein a reference arc is defined between the pressing groove and the round opening, and a ratio of an arc length of the reference arc to a circumference of the round opening is between $1/6$ and $2/5$.

19. The extending assembly as claimed in claim 11, wherein the extending member has a plurality of side through holes, and the plurality of side through holes are arranged mutually parallel to each other at the extending portion and are in communication with the through hole.

20. An assembly method for a device for surgery to stabilize bone segments, the device comprising a screw assembly, at least one supporting member, an extending member, and a fastening member, the screw assembly comprising a receiver having a retainer and two opposite arms, the extending member comprising a connecting portion and at least one extending portion, the extending portion having a through hole, the fastening member having at least one pressing groove, the assembly method comprising the following steps:

providing the screw assembly having the supporting member, wherein the supporting member is connected to one of the two arms and extends in a longitudinal axis direction of the device;

providing the extending portion to be connected to the two arms with the supporting member passing through the through hole, wherein a portion of the supporting member protrudes out of the extending portion to the connecting portion;

providing the fastening member to be sleeved on the connecting portion, wherein the supporting member is located between the connecting portion and the pressing groove; and rotating the fastening member relative to the connecting portion, and moving the supporting member relative to the fastening member to be moved along the pressing groove between the release position and the pressing position, wherein when the supporting member is gradually approaching the pressing position, the pressing groove provides an inwardly pressing force to the supporting member for pushing the supporting member to move inwardly, so that the supporting member and the connecting portion are pressed to be fixed with respect to each other.

* * * * *